US010745825B2

(12) United States Patent
Szczepanik et al.

(10) Patent No.: US 10,745,825 B2
(45) Date of Patent: *Aug. 18, 2020

(54) ENCRYPTED OPTICAL MARKERS FOR SECURITY APPLICATIONS

(71) Applicant: APDN (B.V.I.) INC., Tortola (VG)

(72) Inventors: Maciej B. Szczepanik, Mount Sinai, NY (US); MingHwa Benjamin Liang, East Setauket, NY (US)

(73) Assignee: APDN (B.V.I.) INC., Tortola (VG)

( * ) Notice: Subject to any disclaimer, the term of this patent is extended or adjusted under 35 U.S.C. 154(b) by 118 days.

This patent is subject to a terminal disclaimer.

(21) Appl. No.: 16/028,176

(22) Filed: Jul. 5, 2018

(65) Prior Publication Data

US 2018/0312998 A1    Nov. 1, 2018

Related U.S. Application Data

(63) Continuation-in-part of application No. 14/661,489, filed on Mar. 18, 2015, now Pat. No. 10,047,282.

(60) Provisional application No. 61/954,950, filed on Mar. 18, 2014.

(51) Int. Cl.

| | | |
|---|---|---|
| *B29C 65/00* | (2006.01) | |
| *B29C 65/48* | (2006.01) | |
| *B29C 71/00* | (2006.01) | |
| *B32B 37/00* | (2006.01) | |
| *B41M 3/14* | (2006.01) | |
| *G07D 7/14* | (2006.01) | |
| *C40B 20/04* | (2006.01) | |
| *G07D 7/1205* | (2016.01) | |
| *B42D 25/00* | (2014.01) | |
| *C09B 11/22* | (2006.01) | |
| *C09B 11/24* | (2006.01) | |
| *C09B 69/10* | (2006.01) | |
| *C09B 11/08* | (2006.01) | |
| *C12Q 1/68* | (2018.01) | |
| *C09B 23/16* | (2006.01) | |
| *C09B 57/10* | (2006.01) | |
| *G07D 7/202* | (2016.01) | |
| *C12Q 1/6876* | (2018.01) | |

(52) U.S. Cl.
CPC .............. *C40B 20/04* (2013.01); *B41M 3/142* (2013.01); *B41M 3/144* (2013.01); *B42D 25/00* (2014.10); *C09B 11/08* (2013.01); *C09B 11/22* (2013.01); *C09B 11/24* (2013.01); *C09B 23/164* (2013.01); *C09B 57/10* (2013.01); *C09B 69/103* (2013.01); *C12Q 1/68* (2013.01); *G07D 7/1205* (2017.05); *G07D 7/14* (2013.01); *G07D 7/205* (2013.01); *B29C 65/4825* (2013.01); *B29C 66/733* (2013.01); *B29C 66/737* (2013.01); *B29C 71/00* (2013.01); *C12Q 1/6876* (2013.01)

(58) Field of Classification Search
CPC ..... B29C 65/48; B29C 65/4825; B29C 65/50; B29C 66/41; B29C 66/45; B29C 66/4724; B29C 66/733; B29C 66/7332; B29C 66/737; B29C 71/00; B29C 71/0009; Y10T 436/16; B41M 3/14; B41M 3/142; B41M 3/144; D21H 21/44; D21H 21/46; D21H 21/48; Y10S 428/916; C12Q 2563/185; B42D 25/29; B42D 2035/34; B42D 25/378; G07D 7/14; C09K 11/06
USPC .... 156/60, 63, 64, 67, 153, 272.2, 277, 293, 156/297, 298, 299, 314; 427/7, 145, 157, 427/256
See application file for complete search history.

(56) References Cited

U.S. PATENT DOCUMENTS

| | | |
|---|---|---|
| 4,183,989 A | 1/1980 | Tooth |
| 4,278,557 A | 7/1981 | Elwell, Jr. |
| 4,454,171 A | 6/1984 | Diggle, Jr. et al. |
| 4,548,955 A | 10/1985 | Okahata et al. |
| 4,683,195 A | 7/1987 | Mullis et al. |
| 4,683,202 A | 7/1987 | Mullis |
| 4,736,425 A | 4/1988 | Jalon |
| 4,739,044 A | 4/1988 | Stabinsky |
| 4,757,141 A | 7/1988 | Fung et al. |
| 4,861,620 A | 8/1989 | Azuma et al. |
| 4,965,188 A | 10/1990 | Mullis et al. |
| 5,047,519 A | 9/1991 | Hobbs, Jr. et al. |
| 5,075,216 A | 12/1991 | Innis et al. |

(Continued)

FOREIGN PATENT DOCUMENTS

| | | |
|---|---|---|
| DE | 2518871 A1 | 11/1975 |
| DE | 4443660 C1 | 10/1995 |

(Continued)

OTHER PUBLICATIONS

Kim, Jeong AH et al., "Fabrication and Characterization of a PDMS-Glass Hybrid Continuous-Flow PCR Chip", Biochemical Engineering Journal, 29, 91-97 (2006).

(Continued)

*Primary Examiner* — Philip C Tucker
*Assistant Examiner* — Brian R Slawski
(74) *Attorney, Agent, or Firm* — Clay D. Shorrock

(57) ABSTRACT

Encrypted markers that are not readily detectable can be revealed by treatment with a specific reagent used as a developer to reveal a readily detectable physical property of the marker, such as a characteristic fluorescence emission after excitation with a particular excitation wavelength, or to reveal a visible color. The encrypted marker can be developed in situ, or a sample can be removed by brushing, scraping, swabbing or scratching the marked object or item and developing the encrypted marker or a sample thereof with the appropriate developer to reveal an overt marker or optical signal. The encrypted marker may include a DNA taggant.

19 Claims, No Drawings

(56) References Cited

U.S. PATENT DOCUMENTS

| | | |
|---|---|---|
| 5,089,691 A | 2/1992 | Morisaki et al. |
| 5,132,242 A | 7/1992 | Cheung |
| 5,139,812 A | 8/1992 | Lebacq |
| 5,151,507 A | 9/1992 | Hobbs, Jr. et al. |
| 5,156,765 A | 10/1992 | Smrt et al. |
| 5,176,203 A | 1/1993 | Larzul |
| 5,270,183 A | 12/1993 | Corbett et al. |
| 5,415,839 A | 5/1995 | Zaun et al. |
| 5,429,952 A | 7/1995 | Garner et al. |
| 5,451,505 A | 9/1995 | Dollinger |
| 5,498,283 A | 3/1996 | Botros et al. |
| 5,508,197 A | 4/1996 | Hansen et al. |
| 5,595,871 A | 1/1997 | DelVecchio et al. |
| 5,599,578 A | 2/1997 | Butland |
| 5,602,381 A | 2/1997 | Hoshino et al. |
| 5,639,603 A | 6/1997 | Dower et al. |
| 5,643,728 A | 7/1997 | Slater et al. |
| 5,736,314 A | 4/1998 | Hayes et al. |
| 5,763,176 A | 6/1998 | Slater et al. |
| 5,776,713 A | 7/1998 | Garner et al. |
| 5,849,208 A | 12/1998 | Hayes et al. |
| 5,866,336 A | 2/1999 | Nazarenko et al. |
| 5,912,257 A | 6/1999 | Prasad et al. |
| 5,942,444 A | 8/1999 | Rittenburg et al. |
| 5,956,172 A | 9/1999 | Downing |
| 5,977,436 A | 11/1999 | Thomas et al. |
| 5,989,823 A | 11/1999 | Jayasena et al. |
| 6,013,789 A | 1/2000 | Rampal |
| 6,030,657 A | 2/2000 | Butland et al. |
| 6,033,880 A | 3/2000 | Haff et al. |
| 6,057,370 A | 5/2000 | Weiland et al. |
| 6,127,120 A | 10/2000 | Graham et al. |
| 6,132,996 A | 10/2000 | Hunicke-Smith |
| 6,140,075 A | 10/2000 | Russell et al. |
| 6,169,174 B1 | 1/2001 | Hasegawa et al. |
| 6,261,809 B1 | 7/2001 | Bertling et al. |
| 6,287,768 B1 | 9/2001 | Chenchik et al. |
| 6,312,911 B1 | 11/2001 | Bancroft et al. |
| 6,326,489 B1 | 12/2001 | Church et al. |
| 6,342,359 B1 | 1/2002 | Lee et al. |
| 6,361,944 B1 | 3/2002 | Mirkin et al. |
| 6,379,897 B1 | 4/2002 | Weidenhammer et al. |
| 6,399,397 B1 | 6/2002 | Zarling et al. |
| 6,537,747 B1 | 3/2003 | Mills, Jr. et al. |
| 6,537,752 B1 | 3/2003 | Astle |
| 6,576,422 B1 | 6/2003 | Weinstein et al. |
| 6,608,228 B1 | 8/2003 | Cumpston et al. |
| 6,613,560 B1 | 9/2003 | Tso et al. |
| 6,632,653 B1 | 10/2003 | Astle |
| 6,686,149 B1 | 2/2004 | Sanchis et al. |
| 6,703,228 B1 | 3/2004 | Landers et al. |
| 6,709,692 B2 | 3/2004 | Sudor |
| 6,743,640 B2 | 6/2004 | Whitten et al. |
| 6,995,256 B1 | 2/2006 | Li et al. |
| 7,014,113 B1 | 3/2006 | Powell et al. |
| 7,015,030 B1 | 3/2006 | Fouillet et al. |
| 7,031,927 B1 | 4/2006 | Beck et al. |
| 7,060,874 B2 | 6/2006 | Wilkins |
| 7,112,616 B2 | 9/2006 | Takizawa et al. |
| 7,115,301 B2 | 10/2006 | Sheu et al. |
| 7,133,726 B1 | 11/2006 | Atwood et al. |
| 7,160,996 B1 | 1/2007 | Cook |
| 7,223,906 B2 | 5/2007 | Davis |
| 7,250,195 B1 | 7/2007 | Storey et al. |
| 7,709,250 B2 | 5/2010 | Corbett et al. |
| 7,732,492 B2 | 6/2010 | Makino et al. |
| 8,278,807 B2 | 10/2012 | Agneray et al. |
| 8,597,549 B2 | 12/2013 | Cumpston et al. |
| 9,266,370 B2 | 2/2016 | Jung et al. |
| 9,297,032 B2 | 3/2016 | Jung et al. |
| 2001/0039018 A1 | 11/2001 | Matson et al. |
| 2002/0048822 A1 | 4/2002 | Rittenburg et al. |
| 2002/0051969 A1 | 5/2002 | Goto et al. |
| 2002/0056147 A1 | 5/2002 | Dau et al. |
| 2002/0064639 A1 | 5/2002 | Rearick et al. |
| 2002/0080994 A1 | 6/2002 | Lofgren et al. |
| 2002/0119485 A1 | 8/2002 | Morgan |
| 2002/0128234 A1 | 9/2002 | Hubbell et al. |
| 2002/0129251 A1 | 9/2002 | Itakura et al. |
| 2002/0137893 A1 | 9/2002 | Burton et al. |
| 2002/0155490 A1 | 10/2002 | Skinner et al. |
| 2002/0160360 A1 | 10/2002 | Chenchik et al. |
| 2002/0167161 A1 | 11/2002 | Butland |
| 2002/0185634 A1 | 12/2002 | Marder et al. |
| 2002/0187263 A1 | 12/2002 | Sheu et al. |
| 2003/0000225 A1 | 1/2003 | Nagai et al. |
| 2003/0017551 A1 | 1/2003 | Parthasarathy et al. |
| 2003/0035917 A1 | 2/2003 | Hyman |
| 2003/0064507 A1 | 4/2003 | Gallagher et al. |
| 2003/0096273 A1 | 5/2003 | Gagna |
| 2003/0142704 A1 | 7/2003 | Lawandy |
| 2003/0142713 A1 | 7/2003 | Lawandy |
| 2003/0162296 A1 | 8/2003 | Lawandy |
| 2003/0177095 A1 | 9/2003 | Zorab et al. |
| 2003/0203387 A1 | 10/2003 | Pelletier |
| 2003/0207331 A1 | 11/2003 | Wilson, Jr. et al. |
| 2004/0063117 A1 | 4/2004 | Rancien et al. |
| 2004/0071718 A1 | 4/2004 | Tsai |
| 2004/0115796 A1 | 6/2004 | Burns |
| 2004/0166520 A1 | 8/2004 | Connolly |
| 2004/0219287 A1 | 11/2004 | Regan et al. |
| 2005/0008762 A1 | 1/2005 | Sheu et al. |
| 2005/0019603 A1 | 1/2005 | Kathirgamanathan |
| 2005/0031120 A1 | 2/2005 | Samid |
| 2005/0045063 A1 | 3/2005 | Niggemann et al. |
| 2005/0053968 A1 | 3/2005 | Bharadwaj et al. |
| 2005/0059029 A1 | 3/2005 | Mariella, Jr. et al. |
| 2005/0059059 A1 | 3/2005 | Liang |
| 2005/0112610 A1 | 5/2005 | Lee et al. |
| 2005/0142565 A1 | 6/2005 | Samper et al. |
| 2005/0214532 A1 | 9/2005 | Kosak et al. |
| 2005/0260609 A1 | 11/2005 | Lapidus |
| 2006/0017957 A1 | 1/2006 | Degott et al. |
| 2006/0017959 A1 | 1/2006 | Downer et al. |
| 2006/0117465 A1 | 6/2006 | Willows et al. |
| 2006/0121181 A1 | 6/2006 | Sleat et al. |
| 2006/0199196 A1 | 9/2006 | O'Banion et al. |
| 2006/0286569 A1 | 12/2006 | Bar-Or et al. |
| 2007/0012784 A1 | 1/2007 | Mercolino |
| 2007/0026239 A1 | 2/2007 | Sigrist et al. |
| 2007/0048761 A1 | 3/2007 | Reep et al. |
| 2007/0072197 A1 | 3/2007 | Rayms-Keller et al. |
| 2007/0117119 A1 | 5/2007 | Akita et al. |
| 2007/0121937 A1 | 5/2007 | Kochevar et al. |
| 2007/0254292 A1 | 11/2007 | Fukasawa et al. |
| 2008/0038813 A1 | 2/2008 | Chen |
| 2008/0081357 A1 | 4/2008 | Kwon et al. |
| 2008/0149713 A1 | 6/2008 | Brundage |
| 2008/0153135 A1 | 6/2008 | Liu |
| 2008/0216255 A1 | 9/2008 | Poovey et al. |
| 2008/0248948 A1 | 10/2008 | Hartlep |
| 2008/0290649 A1 | 11/2008 | Klein et al. |
| 2008/0293052 A1 | 11/2008 | Liang et al. |
| 2008/0299559 A1 | 12/2008 | Kwok et al. |
| 2008/0299667 A1 | 12/2008 | Kwok et al. |
| 2008/0312427 A1 | 12/2008 | Kwok et al. |
| 2009/0042191 A1 | 2/2009 | Hayward et al. |
| 2009/0057147 A1 | 3/2009 | Kayyem |
| 2009/0069199 A1 | 3/2009 | Brandenburg |
| 2009/0075261 A1 | 3/2009 | Hayward et al. |
| 2009/0136163 A1 | 5/2009 | Kerr et al. |
| 2009/0220789 A1 | 9/2009 | DeSimone et al. |
| 2009/0222912 A1 | 9/2009 | Boschin |
| 2009/0253127 A1 | 10/2009 | Gaudreau et al. |
| 2009/0286250 A1 | 11/2009 | Hayward et al. |
| 2009/0311555 A1 | 12/2009 | Badyal et al. |
| 2009/0313740 A1 | 12/2009 | Santos et al. |
| 2009/0325234 A1 | 12/2009 | Gregg et al. |
| 2010/0050344 A1 | 3/2010 | Peltz et al. |
| 2010/0065463 A1 | 3/2010 | Taylor |
| 2010/0075407 A1 | 3/2010 | Duffy et al. |
| 2010/0075858 A1 | 3/2010 | Davis et al. |
| 2010/0099080 A1 | 4/2010 | Church et al. |
| 2010/0149531 A1 | 6/2010 | Tang |

(56) References Cited

U.S. PATENT DOCUMENTS

| | | |
|---|---|---|
| 2010/0240101 A1 | 9/2010 | Lieberman et al. |
| 2010/0250616 A1 | 9/2010 | Kim |
| 2010/0258743 A1 | 10/2010 | Bortolin |
| 2010/0267091 A1 | 10/2010 | Murray et al. |
| 2010/0279282 A1 | 11/2010 | Liang et al. |
| 2010/0285447 A1 | 11/2010 | Walsh et al. |
| 2010/0285490 A1 | 11/2010 | Dees et al. |
| 2010/0285985 A1 | 11/2010 | Liang et al. |
| 2010/0307120 A1 | 12/2010 | Stover |
| 2011/0054938 A1 | 3/2011 | Hood et al. |
| 2011/0165569 A1 | 7/2011 | Macula |
| 2011/0229881 A1 | 9/2011 | Oshima et al. |
| 2011/0250594 A1 | 10/2011 | Liang et al. |
| 2011/0263688 A1 | 10/2011 | Barany et al. |
| 2012/0115154 A1 | 5/2012 | Hampikian |
| 2012/0264742 A1 | 10/2012 | Furuishi et al. |
| 2013/0040150 A1 | 2/2013 | Trexler et al. |
| 2013/0040381 A1 | 2/2013 | Gregg et al. |
| 2013/0046994 A1 | 2/2013 | Shaw |
| 2013/0048731 A1 | 2/2013 | Flickner et al. |
| 2013/0109596 A1 | 5/2013 | Peterson et al. |
| 2013/0149706 A1 | 6/2013 | Kwok et al. |
| 2013/0234043 A1 | 9/2013 | Hussain et al. |
| 2013/0274129 A1 | 10/2013 | Katzen et al. |
| 2014/0099643 A1 | 4/2014 | Jung et al. |
| 2014/0106357 A1 | 4/2014 | Berrada et al. |
| 2014/0224673 A1 | 8/2014 | Alocilja |
| 2014/0256881 A1 | 9/2014 | Berrada et al. |
| 2014/0272097 A1 | 9/2014 | Jung et al. |
| 2014/0295423 A1 | 10/2014 | Liang et al. |
| 2015/0018538 A1 | 1/2015 | Berrada et al. |
| 2015/0030545 A1 | 1/2015 | Grass et al. |
| 2015/0083797 A1 | 3/2015 | Tran et al. |
| 2015/0104800 A1 | 4/2015 | Lee et al. |
| 2015/0107475 A1 | 4/2015 | Jung et al. |
| 2015/0125949 A1 | 5/2015 | Liss |
| 2015/0133319 A1 | 5/2015 | Fu et al. |
| 2015/0141264 A1 | 5/2015 | Jung et al. |
| 2015/0191799 A1 | 7/2015 | Liang et al. |
| 2015/0232952 A1 | 8/2015 | Sun et al. |
| 2015/0266332 A1 | 9/2015 | Szczepanik et al. |
| 2015/0275271 A1 | 10/2015 | Berrada et al. |
| 2015/0302713 A1 | 10/2015 | Berrada et al. |
| 2015/0304109 A1 | 10/2015 | Tran et al. |
| 2015/0329856 A1 | 11/2015 | Liang et al. |
| 2016/0076088 A1 | 3/2016 | Tran et al. |
| 2016/0102215 A1 | 4/2016 | Hayward et al. |
| 2016/0168781 A1 | 6/2016 | Tran et al. |
| 2016/0246892 A1 | 8/2016 | Murrah et al. |
| 2016/0264687 A1 | 9/2016 | Tran |
| 2016/0326511 A1 | 11/2016 | Berrada et al. |
| 2016/0362723 A1 | 12/2016 | Jung et al. |
| 2017/0021611 A1 | 1/2017 | Jung et al. |

FOREIGN PATENT DOCUMENTS

| | | |
|---|---|---|
| EP | 0623658 A2 | 11/1994 |
| EP | 0477220 B1 | 9/1996 |
| EP | 0840350 A2 | 5/1998 |
| EP | 1063286 A1 | 12/2000 |
| EP | 1231470 A1 | 8/2002 |
| EP | 1237327 A2 | 9/2002 |
| EP | 1403333 A1 | 3/2004 |
| EP | 1847316 A1 | 10/2007 |
| EP | 2428925 A1 | 3/2012 |
| EP | 2444136 A1 | 4/2012 |
| EP | 2444546 A1 | 4/2012 |
| GB | 2319337 A | 5/1998 |
| GB | 2434570 A | 8/2007 |
| JP | 63-503242 | 11/1988 |
| JP | 2009517250 A | 4/2009 |
| RU | 2084535 C1 | 7/1997 |
| RU | 2170084 C1 | 7/2001 |
| WO | 87/06383 A1 | 10/1987 |
| WO | 90/14441 A1 | 11/1990 |
| WO | 92/04469 A2 | 3/1992 |
| WO | 95/02702 A1 | 1/1995 |
| WO | 95/06249 A1 | 3/1995 |
| WO | 97/04392 A1 | 2/1997 |
| WO | 97/45539 A1 | 12/1997 |
| WO | 98/06084 A1 | 2/1998 |
| WO | 98/16313 A1 | 4/1998 |
| WO | 99/45514 A1 | 9/1999 |
| WO | 99/59011 A1 | 11/1999 |
| WO | 00/55609 A2 | 9/2000 |
| WO | 00/61799 A2 | 10/2000 |
| WO | 01/25002 A1 | 4/2001 |
| WO | 01/36676 A2 | 5/2001 |
| WO | 01/99063 A1 | 12/2001 |
| WO | 02/057548 A1 | 7/2002 |
| WO | 02/066678 A2 | 8/2002 |
| WO | 02/084617 A1 | 10/2002 |
| WO | 03/016558 A1 | 2/2003 |
| WO | 03/030129 A2 | 4/2003 |
| WO | 03/038000 A1 | 5/2003 |
| WO | 03/080931 A1 | 10/2003 |
| WO | 2004/025562 A1 | 3/2004 |
| WO | 2004/086323 A1 | 10/2004 |
| WO | WO2004087430 A1 | 10/2004 |
| WO | 2005/075683 A1 | 8/2005 |
| WO | 2005/103226 A2 | 11/2005 |
| WO | WO2005108103 A2 | 11/2005 |
| WO | 2006/109014 A1 | 10/2006 |
| WO | WO2007037586 A1 | 4/2007 |
| WO | 2007/078833 A2 | 7/2007 |
| WO | 2008/007060 A1 | 1/2008 |
| WO | 2008045288 A2 | 4/2008 |
| WO | 2008/154931 A1 | 12/2008 |
| WO | 2012/076021 A1 | 6/2012 |
| WO | 2013/052924 A1 | 4/2013 |
| WO | 2013/154943 A1 | 10/2013 |
| WO | 2013/170009 A1 | 11/2013 |
| WO | 2014/062754 A1 | 4/2014 |

OTHER PUBLICATIONS

Curcio, Mario et al., "Continuous Segmented-Flow Poymerase Chain Reaction for High-Throughput Miniaturized DNA Amplification" Analytical Chemistry, vol. 75, No. 1, 1-7 ( Jan. 1, 2003).

Kopp, Martin U. et al, "Chemical Amplification: Continuous-Flow PCR on a Chip", Science, vol. 280, 1046-1048 (1998).

Skirtach, Andre, G. et al, "The Role of Metal Nanoparticles in Remote Release of Encapsulated Materials", Nano Letters, vol. 5, No. 7, 1371-1377 (2005).

Fixe, F. et al., Thin Film Micro Arrays with Immobilized DNA for Hybridization Analysis, Mat. Res. Soc. Symp. Proc. vol. 723, Materials Research Society, O2.3.1-O2.3.6 (2002).

Hayward, Jim et al., "A Scaled, Integrative Implementation for DNA Marking of Integrated Circuits", Applied DNA Sciences, 1-25 (2013).

Ovsianikov, Aleksandr et al., "Two-Photon Polymerization Technique for Microfabrication of CAD-Designed 3D Scaffolds from Commercially Available Photosensitive Materials", Journal of Tissue Engineering and Regenerative Medicine, 1:443-449 (2007).

Khandjian, E.W., "Optimized Hybridization of DNA Blotted and Fixed to Nitrocellulose and Nylon Membranes" Biotechnology, vol. 5, 165-167 (1987).

Chrisey, Linda A et al., "Fabrication of Patterned DNA Surfaces", Nucleic Acids Research, vol. 24, No. 15, 3040-3047 (1996).

Wollenberger, Louis V. et al., "Detection of DNA Using Upconverting Phosphor Reporter Probes", SPIE, vol. 2985, 100-111 (1997).

Takara Bio, "Takara Bio to Produce DNA Fragments for DNA Microarrays on Industrial Scale", http://www.evaluategroup.com/Universal/View.aspx?type_Story&id.

Obeid, Pierre J. et al., "Microfabricated Device for DNA and RNA Amplification by Continuous-Flow Polymerase Chain Reaction and Reverse Transcription-Polymerase Chain Reaction with Cycle Number Section", Anal. Chem, 75, 288-295 (2003).

Supplemental European Search Report for Corresponding European Patent Application No. EP14820538.8, pp. 1-8 , (dated Jan. 25, 2017).

(56) References Cited

OTHER PUBLICATIONS

Hashimoto, Masahiko et al., "Rapid PCR in a Continuous Flow Device", Lab Chip, 4, 638-645 (2004).
Thibaudau, Franck, "Ultrafast Photothermal Release of DNA from Gold Nanoparticles", J. Phys. Chem. Lett. 3, 902-907 (2012).
Berger, S.A. et al., "Flow in Curved Pipes", Ann. Rev. Fluid Mech., 15:461-512 (1983).
Written Opinion of the International Search Authority for PCT/US2015/013084 dated Apr. 17, 2015.
Ageno, M., et al., "The Alkaline Denaturation of DNA", Biophys J., Nov. 1969; 9(11): 1281-1311.
Hou, Sen, et al., "Method to Improve DNA Condensation Efficiency by Alkali Treatment", Taylor & Francis, Nucleosides, Nucleotides and Nucleic Acids, 28:725-735, 2009.
Thiel, Teresa, et al., "New zwitterionic butanesulfonic acids that extend the alkaline range of four families of good buffers: Evaluation for use in biological systems", J. Biochem. Biophys., Methods 37 (1998) 117-129.
Schulz, M.M., et al., "Archived or directly swabbed latent fingerprints as a DNA source for STR typing", Forensic Science International 127 (2002) 128-130.
Park, H., et al., "Stress response of fibroblasts adherent to the surface of plasma-treated poly(lactic-co-glycolic acid) nanofiber matrices", Colloids Surf B Biointerfaces, May 1, 2010,1;77(1); 90-5.
WiseGeek, "How Many Species of Bacteria Are There", http://www.wisegeek.org/how-many-species-of-bacteria-are-there.htm.
Wikipedia, "List of sequenced bacterial genomes", http://en.wikipedia.org/wiki/List_of_sequenced_bacterial_genomes.
Wikipedia, "Virus", http://en.wikipedia.org/wiki/Virus.
Agrawal, Sudhir, et al., "Site-Specific Functionalization of Oligodeoxynucleotides for Non-Radioactive Labelling", Tetrahedron Letters, vol. 31, No. 11, pp. 1543-1546, 1990.
Beija, Mariana, et al., "Synthesis and applications of Rhodamine derivatives as fluorescent probes", Chem. Soc. Rev., 2009, 38, 2410-2433.
Corstjens, P.L.A.M., et al., "Infrared up-converting phosphors for bioassays", IEE Proc.—Nanobiotechnol., vol. 152, No. 2, Apr. 2005.
Tyagi, Sanjay, et al., "Multicolor molecular beacons for allele discrimination", Nature Biotechnology, vol. 16, Jan. 1996.
Gibson, U.E., et al., "A novel method for real time quantitative RT-PCR", Genome Res., 1996, 6:995-1001.
Gupta, K.C., et al., "A general method for the synthesis of 3'-sulfhydryl and phosphate group containing oligonucleotides", Nucleic Acids Research, vol. 19, No. 11, p. 3019-3025 (1991).
Heid, C.A., et al., "Real time quantitative PCR", Genome Res. 1996 6:986-994.
Holland, Pamela, M., et al., "Detection of specific polymerase chain reaction product by utilizing the 5'→ 3' exonuclease activity of Thermus aquaticus DNA polymerase", Proc. Natl. Acad. Sci. USA, vol. 88, pp. 7276-7280, Aug. 1991, Biochemistry.
Hosokawa, Kazuo, et al., "DNA Detection on a Power-free Microchip with Laminar Flow-assisted Dendritic Amplification", Analytical Sciences, Oct. 2010, vol. 26.
Hussein, Ebtissam, H.A., et al., "Molecular Characterization of Cotton Genotypes Using PCR-based Markers", Journal of Applied Sciences Research, 3(10): 1156-1169, 2007.

Ibrahim, Rashid Ismael Hag, et al., "Complete Nucleotide Sequence of the Cotton (*Gossypium barbadense* L.) Chloroplast Genome with a Comparative Analysis of Sequences among 9 Dicot Plants", Genes Genet. Syst. (2006) 81, p. 311-321.
Jiang, Chun-Xiao, et al., "Polyploid formation created unique avenues for response to selection in *Gossypium* (cotton)", Proc. Natl. Acad. Sci. USA, vol. 95, pp. 4419-4424, Apr. 1998.
Kaneda, Shohei, et al., "Modification of the Glass Surface Property in PDMS-Glass Hybrid Microfluidic Devices", Analytical Sciences, Jan. 2012, vol. 28.
Karahan, H.A., et al., "Improvements of Surface Functionality of Cotton Fibers by Atmospheric Plasma Treatment", Fibers and Polymers 2008, vol. 9, No. 1, 21-26.
Lee, Seung-Bum, et al., "The complete chloroplast genome sequence of Gossypium hirsutum: organization and phylogenetic relationships to other angiosperms", BMC Genomics 2006, 7:61.
Lee, Linda G., et al., "Allelic discrimination by nick-translation PCR with fluorogenic probes", Nucleic Acids Research, 1993, vol. 21, No. 16, 3761-3766.
Tyagi, Sanjay, et al., "Molecular Beacons: Probes that Fluoresce upon Hybridization", Nature Biotechnology, vol. 18, Mar. 1996.
Sproat, Brian S. et al., "The synthesis of protected 5'-mercapto-2', 5'-dideoxyribonucleoside-3'-O-phosphoramidites; uses of 5'-mercapto-oligodeoxyribonucleotides", Nucleic Acids Research, vol. 15, No. 12, 1987.
Nazarenko, I.A., et al., "A closed tube format for amplification and detection of DNA based on energy transfer", Nucleic Acids Research, 1997, vol. 25, No. 12, 2516-2521.
Nelson, Paul S., et al., "Bifunctional oligonucleotide probes synthesized using a novel CPG support are able to detect single base pair mutations", Nucleic Acids Research, vol. 17, No. 18, 1989.
International Preliminary Report on Patentability issued in PCT/US2013/065161 dated Apr. 21, 2015.
Written Opinion of the International Searching Authority issued in PCT/US15/21165 dated Jul. 2, 2015.
Tuzlakoglu, K., et al., "A new route to produce starch-based fiber mesh scaffolds by wet spinning and subsequent surface modification as a way to improve cell attachment and proliferation", Journal of Biomedical Materials Research Part A, 2009, Wiley Periodicals, Inc, p. 369-377.
Zuckermann, Ronald, et al., "Efficient methods for attachment of thiol specific probes to the 3'-ends of synthetic oligodeoxyribonucleotides", Nucleic Acids Research, vol. 15, No. 13, 1987.
Yang, XF, et al., "Fluorimetric determination of hemoglobin using spiro form rhodamine B hydrazide in a micellar medium", Talanta Nov. 12, 2003; 61(4): 439-45.
Ullrich, Thomas, et al., "Competitive Reporter Monitored Amplification (CMA)—Quantification of Molecular Targets by Real Time Monitoring of Competitive Reporter Hybridization", Plos One, Apr. 2012, vol. 7, Issue 4.
Van De Rijke, Frans, et al., "Up-converting phosphor reporters for nucleic acid microarrays", Nature Publishing Group, Nature Biotechnology Mar. 19, 2001, 273-276.
Whitcombe, David, et al., "Detection of PCR products using self-probing amplicons and fluorescence", Nature Biotechnology, vol. 17, Aug. 1999, p. 804-807.
Hunicke-Smith, Scott P., "PCR and Cycle Sequencing Reactions: A New Device and Engineering Model", Dissertation, Stanford University, pp. i-xiv and 1-200, May 1997.

ENCRYPTED OPTICAL MARKERS FOR SECURITY APPLICATIONS

RELATED APPLICATIONS

This application is a continuation-in-part of U.S. application Ser. No. 14/661,489, filed on Mar. 18, 2015, now U.S. Pat. No. 10,047,282, which claims the benefit of U.S. Provisional Application Ser. No. 61/954,950, filed on Mar. 18, 2014, the disclosures of which are incorporated by reference herein in their entirety.

BACKGROUND

Fluorescent markers are useful as identification and security markers, but the advantage of their being readily visualized by irradiating with light of the appropriate excitation wavelength is also a disadvantage in that the fluorescent marker can be easily detected, analyzed and copied, rendering them subject to counterfeiting.

SUMMARY

The present invention provides encrypted markers that are not readily detectable, but can be revealed by treatment with a specific reagent used as a developer to reveal a readily detectable physical property of the marker, such as, for instance a characteristic fluorescence emission after excitation with a particular excitation wavelength, or to reveal a visible color. The encrypted marker can be developed in situ, or a sample can be removed by brushing, scraping, or scratching the marked object or item and developing the encrypted marker or a sample thereof with the appropriate developer to reveal an overt marker or optical signal. The marker can be revealed by exposure of the encrypted marker in situ or a sample thereof to the developer in solution, a spray, a vapor or a solid, such as for example, a powder or granules that include the developer. The marker may include a DNA taggant encoding information about the marked item.

Alternatively, there may be sufficient transfer of the encrypted marker molecules from the marked object or item by simply swiping with a swab carrying the developer, e.g. a swab soaked in a solution of the developer or a swab on which the developer is bound or covalently immobilized. The transferred encrypted marker molecules are then developed on or in the swab, or on the marked object or item. The swab, or the marked object or item, can be readily inspected for the presence of the revealed optical characteristics, such as color or fluorescence with emission at a specific wavelength after excitation with the appropriate wavelength of light.

The developer can be a chemically reactive developer that reacts with the marker to produce a detectable marker product, or the developer can be a chelating agent or other binding agent that in combination with the marker produces a detectable marker product. In another embodiment, the developer can be an ion, such as for instance, a metal ion that is bound by the marker to produce a detectable marker product.

In one embodiment, the marker of the present invention is an "encrypted fluorophore" (also referred to herein as a "pro-fluorophore") and does not have the properties of a fluorophore and is thus difficult to recognize as a security marker, but on development or reaction with a developer, which is a specific reagent suitable for development of the pro-fluorophore, is transformed into a fluorophore with a readily detectable signal. Additionally, encryption often improves the physical and chemical stability of the pro-fluorophore.

In another embodiment, the chromogenic markers (also referred to herein as "chromogens" or "pro-chromophores") of the present invention are "encrypted chromophores" and are colorless or almost colorless, and are thus difficult to recognize as security markers, but on development or reaction with a developer, a specific reagent, are transformed into a readily detectable chromophore. In one embodiment, the chromophores of the invention are made visible to the naked eye after development of the respective chromogenic markers with the developer reagent specific to the chromogenic marker.

In another embodiment, the markers of the present invention combine the features of both encrypted fluorophores and encrypted chromophores, wherein the encrypted fluorophores are non-fluorescent or essentially non-fluorescent and the encrypted chromophores are colorless or essentially colorless, making them difficult to detect or recognize as security markers. However, on development or reaction with a developer, these encrypted markers are transformed into a readily detectable fluorophore and a readily detectable chromophore. In one embodiment, such a combination marker can be simultaneously interrogated for fluorescence with UV light of an appropriate excitation wavelength, as well as for color visible to the naked eye by visual inspection of the illuminated marker after development with an appropriate developer.

In another embodiment, the pro-fluorophore, chromogenic compound, or combination thereof may be combined with DNA suspended in an aqueous or non-aqueous solvent to form a DNA security marker. Preferably, the DNA is a taggant that is double-stranded DNA of a non-naturally occurring sequence that may be readily identifiable. The DNA security marker may also contain a perturbant to assist in recovery of the DNA and/or to physically separate the DNA from the pro-fluorophore and/or chromogenic compounds. The perturbant may be selected from the group consisting of a polyol or a diol or glycol, a starch or a pyrrolidone or a water immiscible compound. A preferred perturbant is polyethylene glycol.

Therefore, in one embodiment, the invention relates to a method for cryptically marking an item, the method including providing a marker wherein the marker is a pro-fluorophore, a chromogen, or a combination thereof being capable of producing a readily detectable fluorophore, chromophore, or combination thereof upon reaction with a developer, and combining the DNA taggant and the marker to form a DNA security marker; attaching the DNA security marker to the item; and thereby providing a cryptically marked item.

In one embodiment, the inventive concept provides a method for cryptically marking an item, wherein the method includes: providing a chromogenic compound as a marker capable of producing a chromophore upon reaction with a developer, and (i) coating the item with a coating comprising the chromogenic marker compound; (ii) attaching a label or indicia comprising the chromogenic marker compound to the item; or (iii) embedding the chromogenic marker compound in at least a portion of the item; and thereby providing a cryptically marked item.

In another embodiment, the inventive concept provides a method for cryptically marking an item, wherein the method includes: providing a pro-fluorophore (also referred to as a cryptic fluorophore) capable of producing a fluorescent compound upon reaction with a developer, and (i) coating the item with a coating comprising the pro-fluorophore; (ii)

attaching a label or indicia comprising the pro-fluorophore to the item; or (iii) embedding the pro-fluorophore in at least a portion of the item; and thereby providing a cryptically marked item.

In one embodiment of the inventive concept, a pro-fluorophore or chromogenic compound is used as a marker on an object to be tracked or authenticated. The marker may be painted, printed, sprayed, bonded, affixed to or embedded in or on the object or item of interest.

The item of interest may be swiped, rubbed or treated with a swab soaked in a solution of a developer, which is a specific reagent, capable of transforming the encrypted fluorophore marker or chromogenic marker compound into a fluorophore or chromophore, respectively, with a readily detectable signal. In one embodiment, the developer may be immobilized on the swab, e.g. by adsorption or by covalent bonding. Alternatively, the item of interest may be directly exposed to the developer in the form of a vapor, a spray or a solution. The development and authentication of the encrypted fluorophore marker or chromogenic marker compound can be performed by any suitable method, such as for instance and without limitation, in a single step wherein the encrypted fluorophore marker or chromogenic marker compound is developed directly in situ in or on the marked object, or in a two-step procedure, wherein the marker is first transferred to a sampling device or swab etc., and then treated with an appropriate developer delivered in the form of a vapor, a spray or a solution, or by sprinkling the sampling device or swab etc. with a powder or granules consisting of or containing the developer.

DETAILED DESCRIPTION

Definitions

Alkyl, as used herein, refers to a saturated branched or straight chain monovalent hydrocarbon radical of a specified number of carbon atoms. Thus, the term alkyl includes, but is not limited to, methyl ($C_1$ alkyl), ethyl ($C_2$ alkyl), propyl ($C_3$ alkyl), isopropyl (also $C_3$ alkyl), n-butyl($C_4$ alkyl), isobutyl (also $C_4$ alkyl), sec-butyl (also $C_4$ alkyl), and t-butyl (also $C_4$ alkyl).

Alkenyl refers to branched or straight chain hydrocarbon radical having at least one double bond between two carbon atoms.

Alkynyl refers to branched or straight chain hydrocarbon radical having at least one triple bond between two carbon atoms.

Cycloalkyl as used herein means a saturated monocyclic, polycyclic or bridged hydrocarbon ring system substituent or linking group. In a substituted cycloalkyl ring, the substituent is bonded to ring carbon atom replacing a hydrogen atom. For example, $C_3$-$C_{10}$ cycloalkyl designates a ring of three to ten carbon atoms, or a ring of three or more carbon atoms wherein the remaining carbon atoms forming one or more alkyl substituents of the ring.

Heterocyclyl as used herein means a saturated, partially unsaturated or unsaturated monocyclic, polycyclic or bridged hydrocarbon ring system substituent or linking group, wherein at least one ring carbon atom has been replaced with a heteroatom such as, but not limited to nitrogen, oxygen, sulfur, selenium, boron or phosphorus. A heterocyclyl ring system can be a ring system having one, two, three or four nitrogen ring atoms, or a ring system having zero, one, two or three nitrogen ring atoms and one oxygen or sulfur ring atom. The heterocyclic ring system can include more than one ring heteroatom. A heterocyclyl substituent is derived by the removal of one hydrogen atom from a single carbon or nitrogen ring atom. Heterocyclyl includes, but is not limited to, furyl, thienyl, 2H-pyrrole, 2-pyrrolinyl, 3-pyrrolinyl, pyrrolidinyl, pyrrolyl, 1,3-dioxolanyl, oxazolyl, thiazolyl, imidazolyl, 2-imidazolinyl, imidazolidinyl, 2-pyrazolinyl, pyrazolidinyl, pyrazolyl, isoxazolyl, isothiazolyl, oxadiazolyl, triazolyl, thiadiazolyl, tetrazolyl, 2H-pyranyl, 4H-pyranyl, pyridinyl, piperidinyl, 1,4-dioxanyl, morpholinyl, 1,4-dithianyl, thiomorpholinyl, pyridazinyl, pyrimidinyl, pyrazinyl, piperazinyl, azepanyl, diazepinyl, indolizinyl, indolyl, isoindolyl, 3H-indolyl, indolinyl, benzo[b]furyl, benzo[b]thienyl, 1H-indazolyl, benzimidazolyl, benzothiazolyl, purinyl, 4H-quinolizinyl, quinolinyl, isoquinolinyl, cinnolinyl, phthalzinyl, quinazolinyl, quinoxalinyl, 1,8-napthyridinyl, pteridinyl, quinuclidinyl.

As noted above, heterocyclyl also includes aromatic heterocycles, such as pyrrolyl, pyrazolyl, imidazolyl, triazolyl, oxazolyl, isoxazolyl, thiazolyl, isothiazolyl, furyl, thienyl, pyridyl, pyrazinyl, pyrimidinyl, and can be optionally substituted, for instance with alkyl. Heterocyclyl also includes bicyclic heterocyclyls with one or both rings having a heteroatom, e.g. imidazopyrazinyl, benzofuranyl, benzodioxolyl, benzothiophenyl, and quinolinyl.

Arylalkyl means an aryl group attached to the end carbon atom of an alkyl group such as, for instance $C_1$-$C_4$ alkyl.

Aryl means an aromatic, unsaturated pi-electron conjugated monocyclic or polycyclic hydrocarbon ring system substituent or linking group of six, eight, ten or fourteen carbon atoms. An aryl group is derived by the removal of one hydrogen atom from a carbon ring atom. Aryl includes, but is not limited to, phenyl, naphthalenyl, azulenyl and anthracenyl.

Halo—means fluoro (—F), chloro (—Cl), bromo (—Br) or iodo (—I).

Carboxyl means a substituent of the formula —COOH.

Hydroxyl means a substituent of the formula —OH.

Cyano means a substituent of the formula —C≡N.

Nitro means a substituent of the formula —NO$_2$.

Oxo means a substituent of the formula =O in which the oxygen atom is double bonded. Amino means a substituent of formula —NH$_2$ or a linking group having the formula —NH—. Alkylamino or dialkylamino means a substituent of the formula —NH-alkyl or —N(alkyl)$_2$, respectively.

Azido means a substituent of the formula —N$_3$ also represented as —N=N$^+$=N$^-$.

Attaching a security marker to an item includes all means of putting the two together including affixing, embedding, coating, painting, printing, spraying, bonding, and combinations thereof.

Compounds useful in the practice of the present invention as marker pro-fluorophores or chromogenic compounds include pro-fluorophore forms of xanthane dyes such as rhodamines, rhodols and fluoresceins, as well as derivatives of coumarin, cyanine and oxazine. The marker is defined as a pro-fluorophore, chromogen, or combination thereof.

The marker may be combined with DNA suspended in an aqueous or non-aqueous solvent to form a DNA security marker. The DNA is preferably a taggant. In one example, the DNA taggant is a double stranded DNA molecule having a length of between about 20 base pairs and about 1000 base pairs. In another example, the DNA taggant is a double-stranded DNA molecule with a length of between about 80 and 500 base pairs. In another example, the DNA taggant is a double-stranded DNA molecule having a length of between about 100 and about 250 base pairs. Alternatively, the DNA taggant can be single-stranded DNA of any suitable length, such as between about 20 bases and about 1000 bases; between about 80 bases and 500 bases; or between about 100 bases and about 250 bases. The DNA taggant can be a naturally-occurring DNA sequence, whether isolated from natural sources or synthetic; or the DNA taggant can be a non-naturally occurring sequence produced from natural or synthetic sources. All or a portion of the DNA may comprise an identifiable sequence. The preferred DNA is double-stranded DNA of a non-naturally occurring sequence.

Preferably, the DNA taggant is identifiable by any suitable nucleic acid amplification and/or taggant sequence detection technique. Nucleic acid amplification may be accomplished via any technique known in the art, such as, for example, polymerase chain reaction (PCR), loop mediated isothermal amplification, rolling circle amplification, nucleic acid sequence base amplification, ligase chain reaction, or recombinase polymerase amplification. In addition, any known sequence detection and/or identification technique may be used to detect the presence of the nucleic acid taggant such as, for example, hybridization with a taggant-sequence specific nucleic acid probe, an in situ hybridization method (including fluorescence in situ hybridization: FISH), as well as amplification and detection via PCR, such as quantitative (qPCR)/real time PCR (RT-PCR). Isothermal amplification and taggant sequence detection may also be performed with the aid of an in-field detection device such as the T-16 Isothermal Device manufactured by TwistDX, Limited (Hertfordshire, United Kingdom).

The pro-fluorophores, chromogens, or combination thereof (the marker) are present in a large excess weight by weight (w/w) relative to the DNA taggant. The w/w ratio of DNA taggant to pro-fluorophores, chromogens, or combination thereof may be from about 1:100 to about 1-10,000. The preferable w/w ratio is about 1:800 to 1:5,000.

Additionally, to assist in the recovery of the DNA taggant and/or to create a physical separation between the pro-fluorophores, chromogenic compounds, or combination thereof, and the DNA taggant, a perturbant may be included with the DNA. Examples of perturbants include, but are not limited to, a polyol or a diol or glycol, a starch or a pyrrolidone. The polyol can be any suitable polyol, such as a polyethylene glycol polymer, for instance a PEG 200 i.e. a polyethylene glycol having an average molecular number of 200 ethylene glycol units per chain (such as the PEG200 $M_n$ 200 Product No. P3015, Sigma-Aldrich, St. Louis, Mo.). Alternatively, in another embodiment, the polyethylene glycol can be a PEG 10,000 polyol polymer (such as the PEG10,000 Product No. P3015, $M_n$ 10,000 from Sigma-Aldrich).

Examples of glycols include, but are not limited to, any suitable glycol or diol, such as for instance, ethylene glycol, diethylene glycol, glycerol, methanediol, triethylene glycol, propylene glycol from Sigma-Aldrich, or 1,2-butanediol or 1,4-butanediol from Fluka Analytical. Examples of starches include, but are not limited to, a hydroxypropyl starch such as Zeina® B860 from Grain Processing Corp., Muscatine, Iowa. Pyrrolidones include, but are not limited to, an N-alkyl pyrrolidone, or the caprylyl pyrrolidone surfactant: Surfadone® LP100 available from Ashland Inc., Covington, Ky.

Perturbants may also include any water immiscible compound capable of creating a stable oil-in-water emulsion. Examples of such compounds include mineral oil, hydrocarbons, silicone oils and triglycerides. Prior to incorporation with the pro-fluorophores and/or chromogenic compounds, DNA suspended in an aqueous solution may be mixed with a perturbant to form a stable emulsion.

Preferably the perturbant is present in a composition including the DNA taggant and the pro-fluorophores, chromogenic compounds, or combination in an amount less than 2% w/w of the total composition including the DNA taggant; pro-fluorophores, chromogenic compounds, or combinations thereof; and the perturbant (i.e., w/w of the DNA security marker). Any of the following percentages may be used to represent the value or may be combined to represent a range of values or minima or maxima for the amount of perturbant in the total composition: 2%, 1.5%, 1%, 0.9%, 0.8%, 0.7%, 0.6%, 0.5%, 0.4%, 0.3%, 0.2%, 0.1%, 0.09%, 0.08%, 0.07%, 0.06%, 0.05%, 0.04%, 0.03%, 0.02%, and 0.01%. The perturbant may also be present in a composition including the DNA taggant and the pro-fluorophores, chromogenic compounds, or combination thereof in amount in about 50% to about 80% w/w excess of DNA suspended in an aqueous solution to form a DNA/perturbant emulsion. The DNA/perturbant emulsion is then added to the pro-fluorophores and/or chromogenic compounds.

Scheme I shows the general case of a profluorophore (Pro-FL) also interchangebly referred to herein as a fluorogenic compound, treated with a developer to produce a fluorescent compound (FL*) having a characteristic emission wavelength when stimulated with light of the appropriate excitation wavelength, wherein the emitted light is readily detectable either by eye or by spectroscopic measurement.

General Scheme I

Scheme II shows the general case of a chromogenic compound (CHR-gen) also interchangebly referred to herein as a leuco-form of a chromophore (i.e. a chromogen) treated with a developer to produce a chromophore or dye (CHR*) having a characteristic absorption that is readily detectable either by eye or by spectroscopic measurement.

General Scheme II

Examples of fluorescein derivatives useful in the practice of the present invention as marker pro-fluorophores or chromogenic compounds are derivatives of each of the following compounds: Fluorescein, 5-(and-6-)-Carboxyfluorescein (FAM), 5-(and-6)-4,7,2',7'-Tetrachlorofluorescein (TET), 5-(and-6)-2',4',4,5',7',7-hexachlorofluorescein (HEX), 5-(and-6)-Carboxy-4',5'-Dichloro-2',7'-Dimethoxyfluorescein (JOE), Eosin Y (2',4',5',7'-Tetrabromofluorescein), Eosin B (4',5'-Dibromo-2',7'-dinitrofluorescein), Rose Bengal (4,5,6,7-Tetrachloro-2',4',5',7'-tetraiodofluorescein), Erythrosin (2',4',5',7'-Tetraiodofluorescein), 2,7-Dichlorofluorescein, Yakima Yellow, VIC, NED, and many more well known to those of skill in the art of fluorescent compounds and dyes. These derivatives are generally colorless, or essentially colorless and lack appreciable fluorescence; and can be treated with a suitable developer to produce the fluorescent compound or the dye itself.

Examples of rhodamines useful as marker pro-fluorophores or chromogenic compounds include for instance: derivatives of Tetramethylrhodamine (TRITC), 5-(and-6)-

Carboxytetramethylrhodamine (TAMRA), 5-(and-6)-carboxy-X-rhodamine (ROX), Rhodamine 110 (Xanthylium, 3,6-diamino-9-(2-carboxyphenyl)-, salts), Rhodamine B, Rhodamine 6G, etc.

Examples of oxazines useful as marker pro-fluorophores or chromogenic compounds include derivatives of: Nile Red, Nile Blue, Cresyl Violet and Oxazine 170, etc., which can be treated with a developer to reveal the underivatized Nile Red, Nile Blue, Cresyl Violet or Oxazine 170 marker.

For instance, in one embodiment, the pro-fluorophore can be a xanthane, such as for instance:

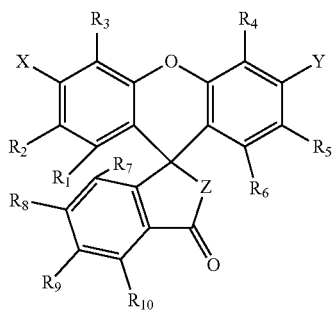

Formula I wherein $R_1$, $R_2$, $R_3$, $R_4$, $R_5$, $R_6$, $R_7$, $R_8$, $R_9$ and $R_{10}$ are each independently selected from hydrogen, halogen (F, Cl, Br, I), nitro ($NO_2$), cyano (CN), carbonyl (CHO or C(O)R), $C_1$-$C_8$ alkyl, aryl, and $C_3$-$C_8$ cycloalkyl, each optionally substituted with one or more functional groups such as carboxyl, carbonyl, amino, cyano, nitro, alkyl, alkenyl, alkynyl or azido.

Alternatively, a pair of R groups independently selected from $R_1$, $R_2$, $R_3$, $R_4$, $R_5$, $R_6$, $R_7$, $R_8$, $R_9$ and $R_{10}$ can form a ring between one another or between $R_n$ (one of $R_1$-$R_{10}$) and either X or Y or both; X and Y are substituted oxygen, X=OR or nitrogen, Y=NRR' wherein substituents R and R' independently selected from hydrogen, $C_1$-$C_8$ alkyl, aryl, $C_1$-$C_8$ acyl (each alkyl, aryl and acyl being optionally substituted with one to three substituents independently selected from halo, nitro ($NO_2$), and $C_1$-$C_3$ alkyl), alkylsulfonyl ($RSO_2$—) and arylsulfonyl ($ArSO_2$—), (wherein the alkylsulfonyl and arylsulfonyl are optionally substituted with one to three substituents independenly selected from halo, nitro ($NO_2$), and $C_1$-$C_3$ alkyl), trialkyl and triarylsilyl; and Z represents oxygen (O), sulfur (S), selenium (Se) or substituted nitrogen (N—R"), wherein R" is defined as for R above; or R" is an amino group, NR'R'", hydroxyl group or OR'", wherein R'" is independently selected from the options for R as defined above.

In one embodiment, the pro-fluorophore (Pro-FL) useful in the practice of the present invention can be prepared from the fluorophore (FL*) by chemical conversions, known in the art, and as depicted in the general Scheme III, as shown below.

General Scheme III

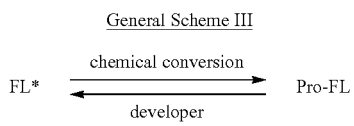

In another embodiment, the said chromogen (CHR-gen) can be prepared from the chromophore (CHR*) by chemical conversions, known in the art, and as depicted in the general Scheme IV, shown below.

General Scheme IV

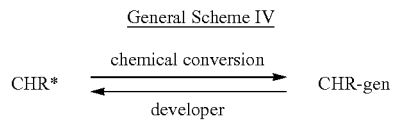

Examples of the above conversions of fluorogen to pro-fluorogen or chromophore to chromogen according to the present invention are depicted in Examples 1, 2 and 6 below.

In another embodiment, the pro-fluorophore can be an oxazine such as for instance:

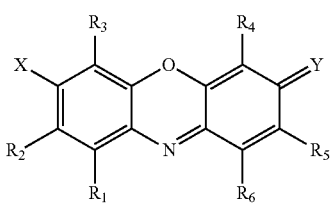

Formula II wherein $R_1$, $R_2$, $R_3$, $R_4$, $R_5$ and $R_6$ are hydrogen, halogen (F, Cl, Br, I), nitro ($NO_2$), cyano (CN), carbonyl (CHO or C(O)R), $C_1$-$C_8$ alkyl, $C_3$-$C_8$ cycloalkyl or aryl. Each of $R_1$, $R_2$, $R_3$, $R_4$, $R_5$ and $R_6$ can also form an optionally substituted ring between one another or between $R_n$ and either X or Y, or both. X and Y are substituted oxygen, X=OR or nitrogen, Y=NRR' wherein substituents R, R' are independently selected from hydrogen, $C_1$-$C_8$ alkyl, aryl and $C_1$-$C_8$ acyl, trialkyl and triarylsilyl; each alkyl, aryl and acyl being optionally substituted with one to three substituents independently selected from halo, nitro ($NO_2$) and $C_1$-$C_3$ alkyl), alkylsulfonyl ($RSO_2$—) and arylsulfonyl ($ArSO_2$—), wherein the alkylsulfonyl and arylsulfonyl are each optionally substituted with one to three substituents independently selected from halo, nitro ($NO_2$) and $C_1$-$C_3$ alkyl.

In another instance, in one embodiment, the pro-fluorophore can be a coumarin such as:

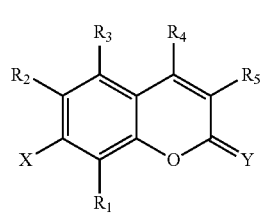

Formula III wherein $R_1$, $R_2$, $R_3$, $R_4$ and $R_5$ are each independently, hydrogen, halogen (F, Cl, Br, I), nitro ($NO_2$), cyano (CN), carbonyl (CHO or C(O)R), $C_1$-$C_8$ alkyl, $C_3$-$C_8$ cycloalkyl, or aryl; wherein each alkyl, aryl and acyl is optionally substituted with one to three substituents independently selected from halo, nitro ($NO_2$) and $C_1$-$C_3$ alkyl), alkylsulfonyl ($RSO_2$—) and arylsulfonyl ($ArSO_2$—), wherein the alkylsulfonyl and arylsulfonyl are each optionally substituted with one to three substituents independently selected from halo, nitro ($NO_2$) and $C_1$-$C_3$ alkyl. $R_1$, $R_2$, $R_3$, $R_4$ and $R_5$ can also form a ring between one another or between $R_n$ and X; wherein X represents substituted oxygen, X=OR or substituted nitrogen, X=NRR' wherein substituents R, R' are independently hydrogen, alkyl, aryl, or $C_1$-$C_8$ acyl, (each alkyl, aryl and acyl being optionally substituted with one to three substituents independently selected from halo, nitro ($NO_2$) and $C_1$-$C_3$ alkyl), alkylsulfonyl ($RSO_2$—) and arylsulfonyl ($ArSO_2$—), wherein the alkylsulfonyl and arylsulfonyl are optionally substituted with one to three substituents independently selected from halo, nitro ($NO_2$), and $C_1$-$C_3$ alkyl groups; trialkyl and triarylsilyl, and Y represents either oxygen (O) or NH.

In another embodiment, the pro-fluorophore can be a compound of Formula IV, as shown below:

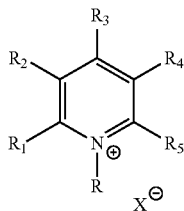

Formula IV wherein $R_1$, $R_2$, $R_3$, $R_4$ and $R_5$ are each independently, hydrogen, halogen (F, Cl, Br, I), nitro ($NO_2$), cyano (CN), $C_1$-$C_8$ alkyl, $C_3$-$C_8$ cycloalkyl, or aryl, each alkyl, cycloalkyl and aryl being optionally substituted with one to three substituents independently selected from halo, nitro ($NO_2$), and $C_1$-$C_3$ alkyl. $R_1$, $R_2$, $R_3$, $R_4$ and $R_5$ can also form a ring between any two of $R_1$, $R_2$, $R_3$, $R_4$ and $R_5$, or between any one of $R_1$, $R_2$, $R_3$, $R_4$ and $R_5$ and the N of Formula IV; and wherein R is hydrogen, $C_1$-$C_8$ alkyl, $C_3$-$C_8$ cycloalkyl, arylalkyl (such as benzyl), or aryl wherein each of the $C_1$-$C_8$ alkyl, $C_3$-$C_8$ cycloalkyl, arylalkyl and aryl are optionally substituted with one to six substituents independently selected from carboxyl (COOH), sulfonate ($SO_3H$) and amino ($NH_2$). X in Formula IV represents a counter-ion exemplified by but not limited to: chloride, bromide, iodide, tosylate, mesylate and perchlorate.

In another embodiment, the pro-fluorophore can be a compound of Formula V, as shown below:

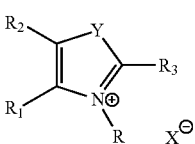

Formula V wherein $R_1$, $R_2$ and $R_3$ are hydrogen, halogen (F, Cl, Br, I), nitro ($NO_2$), $C_1$-$C_8$ alkyl, $C_3$-$C_8$ cycloalkyl, or aryl, each independently optionally substituted with one to three halo, nitro ($NO_2$), $C_1$-$C_3$ alkyl groups. $R_1$, $R_2$ and $R_3$ can also form a cyclic structure between any two of $R_1$, $R_2$ and $R_3$, or between any one of $R_1$, $R_2$ and $R_3$ and N or Y of the heterocycle of formula V; and wherein R is hydrogen, or $C_1$-$C_8$ alkyl, $C_3$-$C_8$ cycloalkyl, arylalkyl (such as benzyl), or aryl, each alkyl, cycloalkyl and arylalkyl being independently optionally substituted. Suitable substituents include but are not limited to carboxyl (COOH), sulfonate ($SO_3H$), and amino ($NH_2$) etc. X represents a suitable counter-ion such as for instance, but not limited to: chloride, bromide, iodide, tosylate, mesylate and perchlorate. Y is oxygen, nitrogen, sulfur, selenium or $C(CH_3)_2$.

In another embodiment of the invention, the pro-fluorophore can be any of the moieties A, $L_1$, $L_2$, $L_3$, $L_4$ in Formula VI (below):

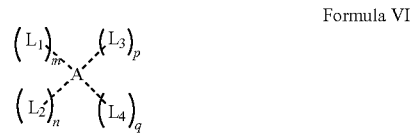

Formula VI

Wherein the sum of m+n+p+q is a positive integer between 1 and 12; m is at least one; and n, p and q are each independently zero or a positive integer. In one embodiment, the complex is formed from A, $L_1$, $L_2$, $L_3$, $L_4$ in Formula VI with or without the assistance of a catalyst or activator as explained below.

Furthermore, $L_1$, $L_2$, $L_3$, $L_4$ can each be different from each other ($L_1 \neq L_2 \neq L_3 \neq L_4$); or two or more of the moieties $L_1$, $L_2$, $L_3$ and $L_4$ can be the same. In one particular embodiment the moieties $L_1$, $L_2$, $L_3$ and $L_4$ are all the same ($L_1=L_2=L_3=L_4$).

The structure represented by Formula VI is a coordination compound such as, for instance, an organometallic compound, where A is a central ion which is chelated by ligands $L_1$, $L_2$, $L_3$, $L_4$. Central ion A and ligands $L_1$, $L_2$, $L_3$, $L_4$ are chosen in such a way that only the combination of A coordinated by ligands $L_1$, $L_2$, $L_3$, $L_4$ will generate a discreet spectroscopic signal manifested by color or fluorescence, or both.

$L_1$, $L_2$, $L_3$, $L_4$ can be any chemical moiety capable of forming coordination bonds with central ion A, via electron pairs available on a nitrogen, oxygen, sulfur or selenium atom of the ligand. One category of the molecules useful in the present invention as a ligand incorporates a heterocyclic compound and derivatives thereof, which may include, but is not limited to a heterocycle selected from: furane, thiophene, pyrrole, oxazole, thiazole, imidazole, pyrazolidinyl, pyrazole, isoxazole, isothiazole, oxadiazole, triazole, thiadiazole, tetrazole, 2H-pyrane, 4H-pyrane, pyridine, bipyridyl, terpyridine, triazine, piperidine, pyrrolidine, 1,4-dioxane, morpholine, 1,4-dithiane, thiomorpholine, pyrazine, pyridazine, pyrimidine, piperazole, azepane, diazepine, indolizine, indole, isoindole, benzimidazole, benzoxazole, benzothiazole, purine, quinolizidine, quinoline, isoquinoline, diazanaphthalenes, pteridine and phenanthroline.

Another category of the ligands L includes polydentate chelators and their derivatives, such as ethylenediaminetetraacetic acid (EDTA), 1,2-bis(2-aminophenoxy)ethane-N,N,N',N'-tetraacetic acid (BAPTA), diethylenetriaminepentaacetic acid (DTPA), triethylenetetramine-N,N,N',N'', N''', N'''-hexaacetic acid (TTHA), N,N,N',N'-tetrakis(2-pyridylmethyl)ethylene-diamine (TPEN), ethylene glycol-bis(2-aminoethylether)-N,N,N',N'-tetraacetic acid (EGTA), 1,4,7,10-tetraazacyclododecane-1,4,7,10-tetraacetic acid (DOTA), 1,4,8,11-tetraazacyclo-tetradecane-5,12-dione dehydrate (5,12-Dioxocyclam), calixarenes (e.g. meso-octamethyl-calix(4)pyrrole, calix[4]arene-25,26,27,28-tetrol, calix[6]arene), crown ethers (e.g. dibenzo-15-crown-5, cyclen), cyclodextrins (e.g. a-cyclodextrin).

Another category of ligands, L, includes but is not limited to β-diketones (e.g. acetylacetone and the derivatives thereof, including hexafluoroacetylacetone; 4,4,4-trifluoro- 1-phenyl-1,3-butanedione; 1,3-diphenyl-1,3-propanedione); Phosphine oxides (e.g. triphenylphosphine oxide, n-trioctylphosphine oxide); aromatic acids and phenols and their derivatives (e.g. tiron, catechol, salicylic acid); Schiff bases and their derivatives (e.g. the 2-phenolsalicylimine depicted in Example 5 below).

Another class of ligands, L, includes solvent molecules. This class is chemically very diverse, and includes several of the compounds mentioned above, such as heterocyclic compounds (pyridine, collidine, furan, tetrahydrofurane (THF) etc.) and crown ethers (15-crown-5 etc.), as well as other molecules representing a broad selections of chemical functionalities. These include, for instance, the following molecules and their derivatives: water, alcohols (methanol, ethanol etc.), amines (triethylamine, diisopropylethylamine, morpholine, dimethylamine, N,N-dimethylaminopyridine (DMAP) etc.), ethers (diethyl ether etc.), polar aprotic solvents (dimethyl sulfoxide (DMSO), dimethylformamide (DMF), dimethylacetamide (DMA), hexamethylphosphoramide (HMPA), 1,3-dimethyl-3,4,5,6-tetrahydro-2(1H)-pyrimidinone (DMPU), 1,3-dimethyl-2-imidazolidinone (DMI), 1-methyl-2-pyrrolidinone (NMP), acetonitrile (AcCN), sulfolane, tetraethylene glycol dimethyl ether (tetraglyme), etc.).

In embodiments of the present invention, central ion A can be any positively charged ion capable of forming a coordination compound with one or more of the ligands, L. One category of the ions, A useful in the practice of the present invention is the category of metal ions, including, but are not limited to, transition metal ions, alkaline and alkaline earth metal ions, lanthanides and actinides.

Central ion A can be provided in a form of an inorganic or organic salt. Suitable inorganic salts include, but are not limited to mineral acid salts such as, sulfates, sulfites, sulfides, nitrates, nitrites, carbonates, borates, phosphates, selenates, fluorides, chlorides, bromides, iodides, chlorates, perchlorates, etc. Suitable organic salts include, but are not limited to organic acid salts such as, monocarboxylic acid salts (e.g. salts of formic, acetic, propionic, butyric, pivalic, 2-ethylhexanoic, palmitic, stearic, oleic, benzoic, salicylic, 4-sulfosalicylic etc. acid), polycarboxylic acid salts (e.g. salts of oxalic, malonic, succinic, glutaric, adipic, citric, trimesic, mellitic etc. acids).

Another class of central ion A includes oxygen atom-containing moieties such as hydroxides and oxides etc.

The choice of the supplied form of central ion A for any particular embodiment of the present invention is dictated by the application (i.e. the object or item to be marked and its environment) and the carrier properties (i.e. the nature of the medium that includes the marker, such as for instance a coating, a paint or a varnish layer).

In one embodiment, the complex is formed from A, $L_1$, $L_2$, $L_3$, $L_4$ in Formula VI with the assistance of a catalyst or activator. The catalysts and activators useful in the practice of the present invention include basic and nucleophilic agents, exemplified but not limited to, simple organic and inorganic bases (hydroxides, amines, alkoxides, phenoxides and the like). This category also comprises inorganic or organic salts of weak acids and strong bases generating upon solvolysis alkaline solutions, e.g. ammonium, alkaline and alkaline earth metal carbonates, bicarbonates, borates, phosphates, acetates etc. Exemplary hydroxides are alkaline and alkaline earth hydroxides such as ammonium, lithium, sodium, potassium, rubidium, cesium, calcium, strontium or barium hydroxide as well as tetraalkylammonium hydroxides, such as tetramethylammonium or tetrabutylammonium hydroxide. Examples of amines useful as catalysts and activators include but are not limited to: triethylamine, diisopropylethylamine, benzylamine, morpholine, pyrrolidine, piperidine, dimethylaminoaniline etc. Examples of alkoxides and phenoxides useful as catalysts and activators include but are not limited to: alkaline alkoxides and phenoxides, such as: sodium or potassium methoxide, ethoxide or phenoxide.

In another embodiment, the catalyst is an acidic substance, as defined by either Bronsted-Lowry or Lewis theory, and can be represented by simple organic or inorganic acid, as well as any inorganic or organic salt of weak base and strong acid generating acidic conditions upon solvolysis, e.g. metal chloride, bromide, nitrate, sulfate etc.

Compounds useful as developers, i.e. decrypting agents in the practice of the present invention include compounds known in the art as good chelators or complexing agents, such as for instance and without limitation:

Heterocyclic aromatic compounds, e.g. imidazoles, phenanthrolines, pirydines, thiazoles and the derivatives thereof;

Polydentate chelators (EDTA, EGTA, BAPTA, DOTA, DTPA);

β-diketones (e.g. acetylacetone and the derivatives thereof, including but not limited to hexafluoroacetylacetone; 4,4,4-trifluoro-1-phenyl-1,3-butanedione; 1,3-diphenyl-1,3-propanedione);

Phosphine oxides (trioctylphosphine oxide; triphenylphosphine oxide);

Aromatic acids and polyphenols (e.g. salicylic acid, catechol, Tiron);

Aromatic aldehydes (e.g. 4-(N,N-dimethylamino)benzaldehyde, 4-(N,N-dimethylamino)cinnamaldehyde, p-anisaldehyde, 4-hydroxybenzaldehyde, etc.)

Schiff bases and derivatives (e.g. 2-phenolsalicyl imine depicted in Example 5 below).

Compounds useful as developers, i.e. decrypting agents in the practice of certain embodiments of the present invention include compounds known in the art as nucleophilic species, involved in solvolysis or deprotection, such as for instance, simple organic and inorganic bases (hydroxides, amines, alkoxides, phenoxides and the like); simple organic and inorganic salts (acetates, sulfides, iodides, fluorides, oxalates, citrates and the like).

Compounds useful as developers, i.e. decrypting agents in the practice of certain embodiments of the present invention also include compounds known in the art as acidic species, involved in solvolysis or deprotection such as simple organic and inorganic acids. In other embodiments, the developer can be an electrophilic species for solvolysis or deprotection, such as for instance, an aldehyde compound, e.g. benzaldehyde or salicyladehyde, or derivatives thereof.

In some specific embodiments the pro-fluorophore or chromogen can be used as the developer and any of the chemical compounds listed above can be used in the coating or embedded in the material marked. The chromogen or pro-fluorophore can then be used as the developer.

In some specific embodiments the developer may require the presence of the catalyst to speed up the decryption reaction of the encrypted fluorophore (which may also be referred to as a pro-fluorophore) or the encrypted chromophore (which may also be referred to as a prochromophore, or a chromogen) and to render the marker useful as a rapid in-field authentication system. The catalysts useful in the practice of the invention include for instance, basic and nucleophilic agents, exemplified but not limited to, simple organic and inorganic bases (hydroxides, amines, alkoxides, phenoxides and the like. In another embodiment, the catalysts can be a simple organic or inorganic acid.

EXAMPLES

1. Pro-Fluorophores

Encrypted pro-fluorophores are hidden/occult fluorophores that are revealed by development with a specific reagent that converts the pro-fluorophore or leuco-form that may be colorless and shows little or no fluorescence to the active fluorophore which may also be intensely colored under visible light.

For instance the compound, rhodamine B hydrazide, a colorless compound can be developed with $Cu^{2+}$ metal ions under acidic conditions to yield a magenta compound with intense orange-red fluorescence. See the reaction illustrated above, showing the conversion of the colorless hydrazide to the magenta copper-coordinated compound by the copper ion, which in turn is slowly hydrolyzed to the colorless carboxylate.

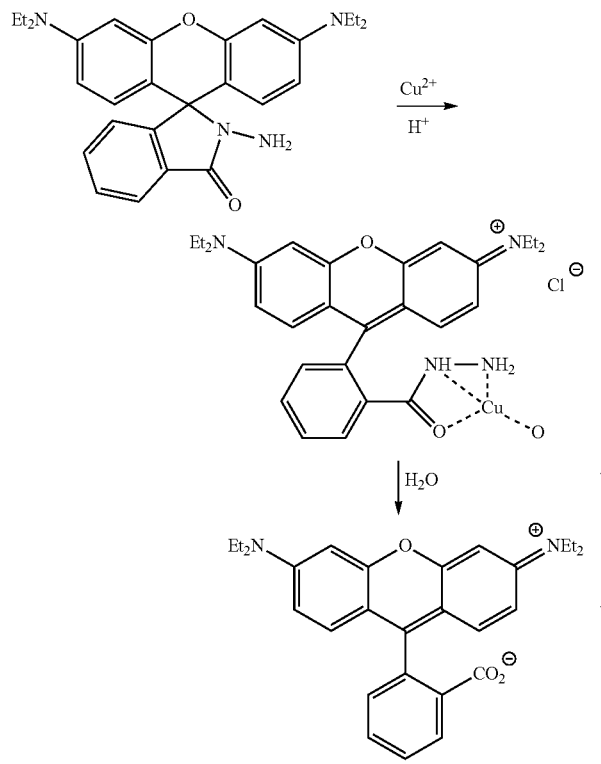

In other examples of profluorophores, the natural properties of susceptibility to a first order hydrolysis reaction can be used as a "time stamp" wherein the rate of decay in air or in a specific carrier under normal conditions is characteristic of the particular encrypted fluorophore. For example, the compound can be a leuco form chosen to be relatively stable in a liquid, such as an ink and decay over a period of weeks to produce a colored and intensely fluorescent form.

2. Two Part Fluorophores

The two part fluorophores are assembled from two non-fluorescent, or very weakly fluorescent components (A) and (B), in some cases in the presence of a catalyst. Only upon reaction of both (A) and (B) components is the actual fluorophore produced. The reaction between both components may also generate colorimetric changes in addition to developing fluorescence. Component (A) of the two part fluorophore can be used as the hidden security/authentication marker and the verification can be achieved by adding the second component (B) to component (A) to produce the active fluorophore. In certain embodiments this process may be enhanced by the addition of a catalyst.

For instance, substituted benzazolium salts can be used as the component (A) and developed with a specific reagent (and an optional catalyst) as exemplified below:

These non-fluorescent components (A) are stable and only revealed by exposure to the appropriate second components (B) and do not spontaneously decrypt over time.

Alternative substituents of the aromatic compounds can be used to change the spectral properties or solubility profile of the fluorophore at the option of the chemist or the designer of the pro-fluorophore as a cryptic marker.

3. Thermostable Pro-Fluorophores

Inorganic elements can be used as thermostable or even fire resistant markers that can be revealed by development with a specific reagent, which can be an organic component. For instance aluminum chloride ($AlCl_3$) can be used as a covert marker that may be incorporated into for example an ink, a lacquer or a varnish and revealed by addition of a specific chelating agent which becomes intensely fluorescent by forming a coordination compound with new spectral properties. In some cases a catalyst may be required to speed the reaction. An example of the formation of an aluminum-based fluorophore from an aluminum chloride ($AlCl_3$) marker is shown below:

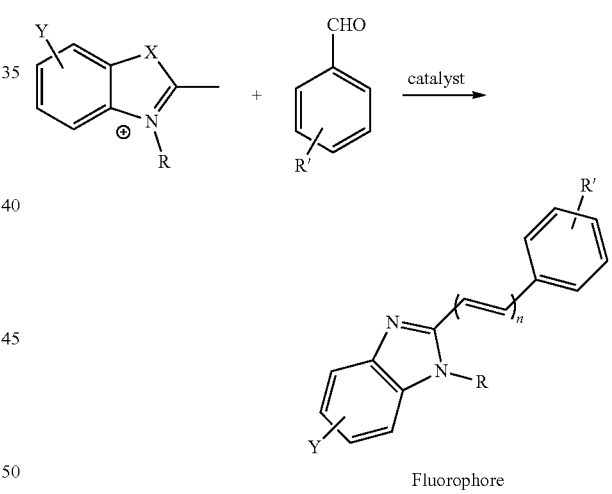

Fluorophore

Other inorganic elements or ions useful as thermostable pro-fluorophores include anions such as phosphate ions, iodide ions, fluoride ions and acetate ions; and cations such as metal ions. Appropriate choice of alternative substituents of the aromatic coordination compounds or chemosensors can be used to change the spectral and other physicochemical properties of the fluorophore at the option of the designer.

4. Polymerizable Encrypted Pro-Fluorophores

Encrypted pro-fluorophores can be rendered polymerizable by addition of appropriate functional groups. Such encrypted pro-fluorophores can be based on excellent fluorophores (bright and with high quantum yields) that are readily and inexpensively synthesized. Pro-chromophores and pro-fluorophores with chromophoric and fluorescence emission properties can be provided, depending on the chromophore or fluorophore template chosen.

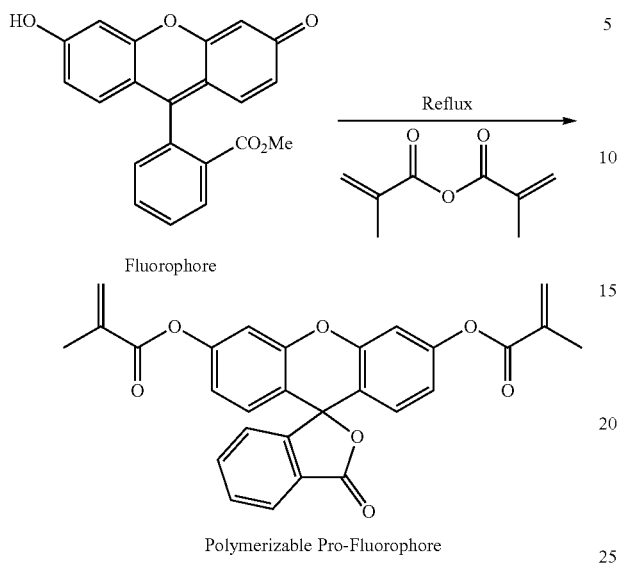

Fluorophore

Polymerizable Pro-Fluorophore

The chemical stability and hydrophobicity of the pro-fluorophores can be controlled by choice of the appropriate acyl groups or aromatic ring substituents.

In one embodiment, the encrypted fluorophores can also be incorporated into nanoparticles containing DNA, such as for instance, and without limitation, lyophilized or encapsulated DNA. Polymerization of the above exemplified polymerizable pro-fluorophore in a methyl-methacrylate polymer is shown below:

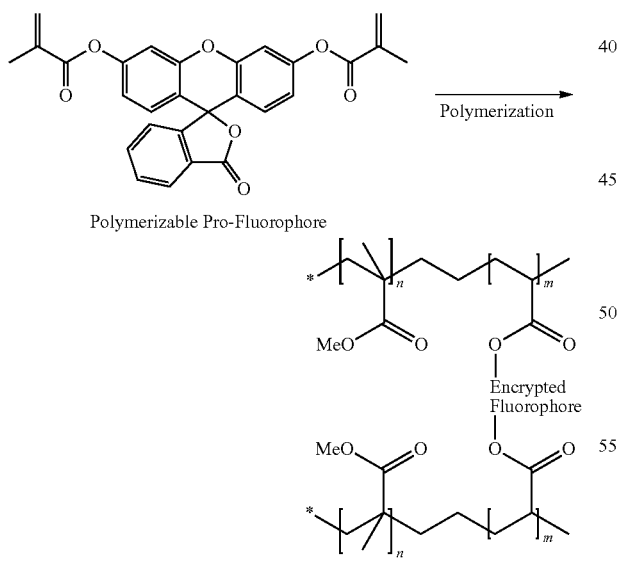

Polymerizable Pro-Fluorophore

Encrypted Fluorophore

Such polymers can be used to encapsulate security markers, such as DNA or other biomolecules, or can be assembled as microparticles or nanoparticles for use as transferable markers, or for incorporation into polymers or other materials with or without entrapped DNA or other detectable marker(s).

The following examples 1-6 are embodiments of the above described compounds useful as encrypted optical markers of the invention.

Example 1: Synthesis of Rhodamine B Hydrazide

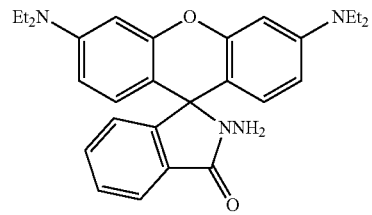

2-amino-3', 6'-bis(diethylamino)spiro[isoindoline-3,9'-xanthane]-1-one

Rhodamine B (479 mg) was dissolved in ethanol and excess of 65% aqueous hydrazine was added to this mixture under vigorous stirring. After refluxing for 2 hours the reaction mixture was cooled and off-white precipitate was collected. The solid was extensively washed with ethanol:water mixture and the 2-amino-3',6'-bis(diethylamino)spiro[isoindoline-3,9'-xanthene]-1-one product was dried in vacuo.

Example 2: Synthesis of Eosin Y Diacetate

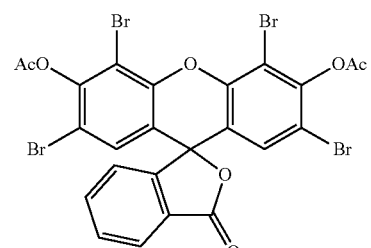

(6'-acetoxy-2',4',5',7'-tetrabromo-3-oxo-spiro[isobenzofuran-1,9'-xanthene]-3'-yl) acetate Eosin Y (648 mg) was suspended in acetic anhydride and the mixture was stirred at reflux for 5 hours. Then the reaction mixture was slowly added to ice-water mixture. The resulting light brown solid was collected and washed with several portion of water. Then the product was dissolved in dimethylformamide (DMF) and precipitated by adding to water. After water wash the solid-acetoxy-2',4',5',7'-tetrabromo-3-oxo-spiro[isobenzofuran-1,9'-xanthene]-3'-yl) acetate product was dried in vacuo.

Example 3: Synthesis of 1,2-Dimethylbenzothiazolium iodide

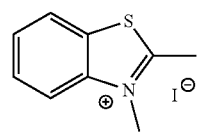

2,3-dimethyl-1,3-benzothiazole hydroidide

To 2-methylbenzothiazole (2.54 ml) in anhydrous toluene iodomethane (2.5 ml) was added in portions. The mixture was refluxed for 6 hours, cooled down to room temperature and then left for several hours at 4° C. Resulting yellow precipitate was collected and washed repeatedly with acetone. The solid 2,3-dimethyl-1,3-benzothiazole hydroiodide product was then dried in vacuo.

Example 4: Synthesis of a Fluorescent Dysprosium Complex

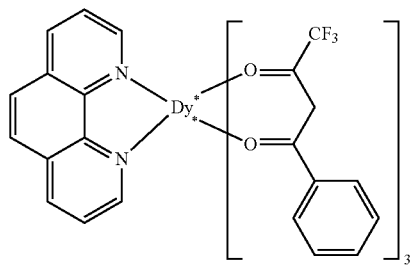

dimethyldysprosium; methyl; RE)-[3-oxo-3-phenyl-1-(trifluoromethyl)propylidene]-3-oxidanyl; 1,10-phenanthroline 4,4,4-Trifluoro-1-phenyl-1,3-butanedione (649 mg) and 1,10-phenanthroline were dissolved in absolute ethanol (3 ml). To this solution aqueous sodium hydroxide (1 M) was added dropwise and the reaction mixture was stirred for 10 min. Separately, dysprosium nitrate hydrate (456 mg) was dissolved in water (1 ml) and the solution was added to the alkaline dione. The reaction mixture was stirred at 60 C for 5 hours to give a white solid form of the dimethyl-dysprosium; methyl; RE)-[3-oxo-3-phenyl-1-(trifluoromethyl)propylidene]-3-oxidanyl]; 1,10-phenanthroline product.

Example 5: Synthesis of 2-Phenolsalicyl imine

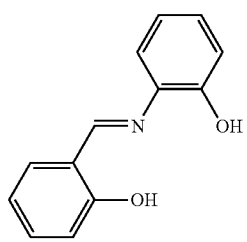

2-[(E)-(2-hydroxyphenyl)iminomethyl]phenol

A solution of 2-hydroxyaniline (2.84 g) in ethanol was added to a solution containing 2-hydroxybenzaldehyde (3.4 g) in ethanol. The mixture was refluxed for 2 hours under nitrogen and then it was cooled to room temperature. The orange 2-[(E)-(2-hydroxyphenyl)iminomethyl]-phenol precipitate was washed with ice cold ethanol and dried in vacuo.

Example 6: Synthesis of Fluorescein Dimethacrylate

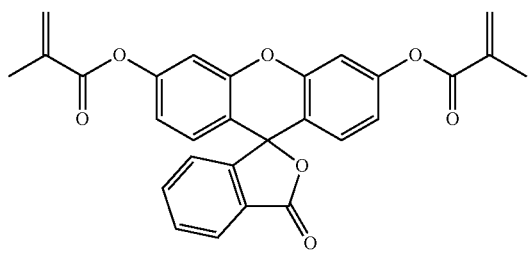

[6'-(2-methylprop-2-enoyloxy)-3-oxo-spiro[isobenzofuran-1,9'-xanthene]-3'-yl]2-methylprop-2-enoate Fluorescein sodium salt (376 mg) was suspended in methacrylic anhydride and the mixture was stirred at reflux for 5 hours. Then the reaction mixture was slowly added to ice-water mixture. Resulting light brown solid was collected and washed with several portion of water. Then the product was dissolved in dimethylformamide and precipitated by adding to water. After water wash the yellow solid 6'-(2-methylprop-2-enoyloxy)-3-oxo-spiro[isobenzofuran-1,9'-xanthene]-3'-yl12-methylprop-2-enoate product was dried in vacuo.

The invention claimed is:

1. A method for cryptically marking an item, the method comprising:
   providing a marker wherein the marker is a pro-fluorophore, a chromogen, or a combination thereof being capable of producing a readily detectable fluorophore, chromophore, or combination thereof upon reaction with a developer, and
   combining a DNA taggant and the marker to form a DNA security marker;
   attaching the DNA security marker to the item; and
   thereby providing a cryptically marked item.

2. The method according to claim 1, wherein the marker is a pro-fluorophore.

3. The method according to claim 1, wherein the marker is a chromogen.

4. The method according to claim 1, wherein the DNA taggant is double-stranded DNA of a non-naturally occurring sequence that is readily identifiable.

5. The method according to claim 1, wherein the DNA taggant has a length of between about 80 and 500 base pairs.

6. The method according to claim 1, wherein the DNA taggant is suspended in an aqueous solution or a non-aqueous solution.

7. The method according to claim 1, wherein the ratio of DNA taggant to marker is about 1:100 to about 1:10,000.

8. The method according to claim 7, wherein the ratio of DNA taggant to marker is about 1:800 to about 1:5,000.

9. The method according to claim 1, wherein the DNA security marker further comprises a perturbant.

10. The method according to claim 9, wherein the perturbant comprises a polyol, a diol, a glycol, a starch, or a pyrrolidone.

11. The method according to claim 10, wherein the perturbant is a polyol and the polyol is polyethylene glycol.

12. The method according to claim 9, wherein the DNA taggant is suspended in an aqueous solution and the perturbant is any water immiscible compound capable of creating a stable oil in water emulsion.

13. The method according to claim 12, wherein the perturbant comprises mineral oil, hydrocarbons, silicone oils, or triglycerides.

14. The method according to claim 9, wherein the perturbant is present in the DNA security marker in an amount of less than 2% w/w.

15. The method according to claim 1, wherein the DNA security marker or developer comprises an anion.

16. The method according to claim 1, wherein the DNA security marker or developer comprises a transition metal ion.

17. The method according to claim 16, wherein the transition metal ion comprises $Cu2\pm$.

18. The method according to claim 1, further comprising developing the marker with the developer to produce a readily detectable fluorophore, chromophore, or combination thereof.

19. The method according to claim 1, wherein the marker comprises a polymerizable monomer capable of polymerizing to form a solid, a layer, a particle, a microparticle or a nanoparticle.

* * * * *